(12) United States Patent
Truhler et al.

(10) Patent No.: US 10,556,091 B2
(45) Date of Patent: Feb. 11, 2020

(54) THREADED, LOCKING HANDLE MECHANISM FOR ATTACHING TO SHAFT

(71) Applicant: St. Jude Medical, Cardiology Division, Inc., St. Paul, MN (US)

(72) Inventors: Maureen Truhler, Oakdale, MN (US); Donald G. Goblish, Minnetonka, MN (US); Bradley C. Knippel, Lino Lakes, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 419 days.

(21) Appl. No.: 15/308,266

(22) PCT Filed: Apr. 30, 2015

(86) PCT No.: PCT/US2015/028465
§ 371 (c)(1),
(2) Date: Nov. 1, 2016

(87) PCT Pub. No.: WO2015/171416
PCT Pub. Date: Nov. 12, 2015

(65) Prior Publication Data
US 2017/0049994 A1 Feb. 23, 2017

Related U.S. Application Data

(60) Provisional application No. 61/989,991, filed on May 7, 2014.

(51) Int. Cl.
*A61M 25/01* (2006.01)
*A61B 18/14* (2006.01)
(Continued)

(52) U.S. Cl.
CPC ......... *A61M 25/0136* (2013.01); *A61B 5/042* (2013.01); *A61B 18/1492* (2013.01);
(Continued)

(58) Field of Classification Search
CPC ...... A61M 2025/0098; A61M 25/0136; A61M 25/0014; A61M 25/0097; A61M 39/12;
(Continued)

(56) References Cited

U.S. PATENT DOCUMENTS 4,323,065 A 4/1982 Kling
4,547,194 A * 10/1985 Moorehead ....... A61M 25/0014
285/24

(Continued)

FOREIGN PATENT DOCUMENTS

FR 2650957 A1 2/1991

*Primary Examiner* — Jonathan P Masinick
(74) *Attorney, Agent, or Firm* — Dykema Gossett PLLC

(57) ABSTRACT

A catheter assembly comprising a catheter handle (101) with a collet (118) disposed at a distal end. The collet is coupled to a strain relief (107) comprising a nut (122) and a strain relief projection (135). The collet comprises at least one leaflet (124, 125) and at least one collet spur (672, 682), and the nut comprises at least one ratchet (251). The collet is configured to couple to the nut, and the at least one ratchet is configured to interact with the at least one collet spur to securely fasten the strain relief to the catheter handle. The at least one leaflet is configured to couple to a catheter shaft.

15 Claims, 14 Drawing Sheets

(51) Int. Cl.
*A61B 5/042* (2006.01)
*A61B 90/00* (2016.01)
*A61B 17/00* (2006.01)

(52) U.S. Cl.
CPC ............... *A61B 2017/0046* (2013.01); *A61B 2017/00424* (2013.01); *A61B 2090/031* (2016.02); *A61M 2205/586* (2013.01)

(58) Field of Classification Search
CPC ... A61B 1/00066; A61B 18/1492; F16B 2/06; F16B 2/065
See application file for complete search history.

(56) References Cited

U.S. PATENT DOCUMENTS

| | | | | |
|---|---|---|---|---|
| 5,047,021 | A | * | 9/1991 | Utterberg ............. A61M 39/10 285/332 |
| 5,224,939 | A | | 7/1993 | Holman et al. |
| 5,395,329 | A | | 3/1995 | Fleischhackor et al. |
| 7,092,765 | B2 | | 8/2006 | Geske et al. |
| 7,930,040 | B1 | | 4/2011 | Kelsch et al. |
| 9,352,118 | B2 | * | 5/2016 | Rowe .................... A61M 39/06 |
| 2013/0138086 | A1 | | 5/2013 | Thor et al. |
| 2014/0276397 | A1 | * | 9/2014 | Terwey ............. A61B 18/1492 604/95.04 |
| 2018/0126142 | A1 | * | 5/2018 | Agrawal ........... A61M 39/0606 |
| 2018/0318571 | A1 | * | 11/2018 | Rieckmann ....... A61M 39/0606 |

* cited by examiner

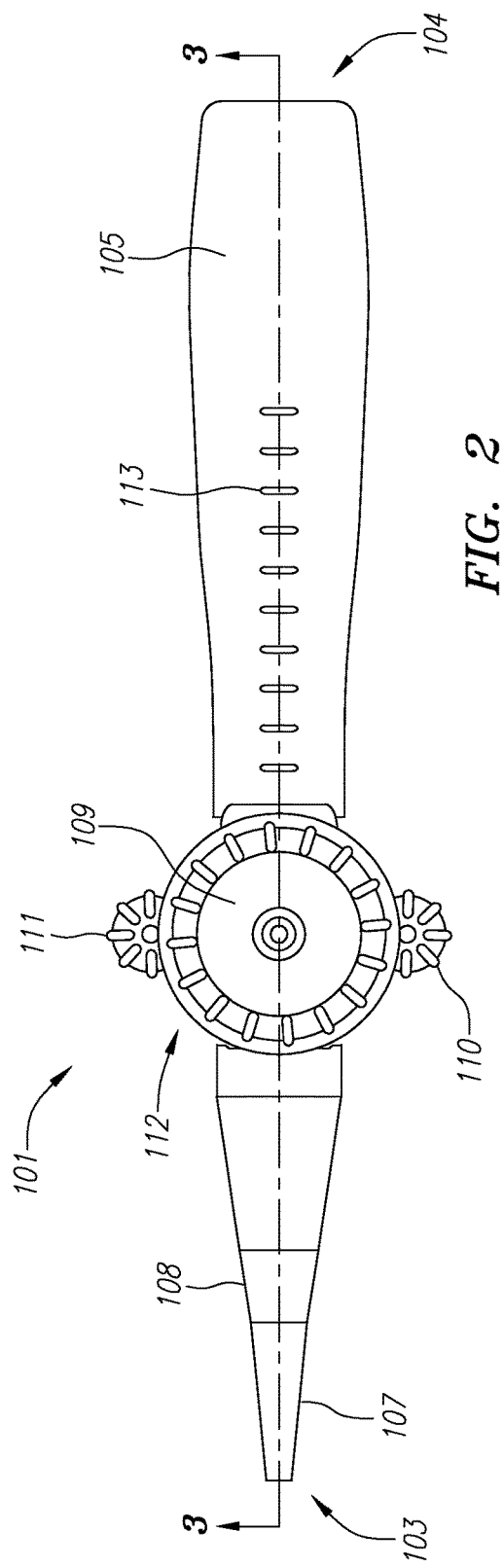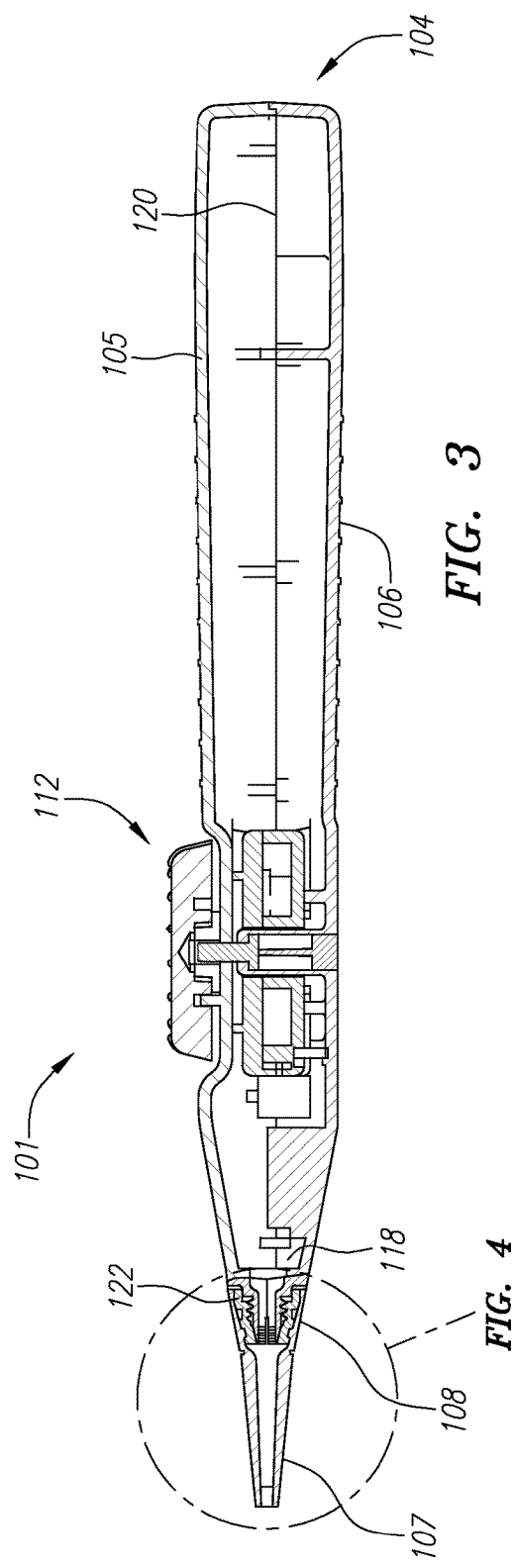

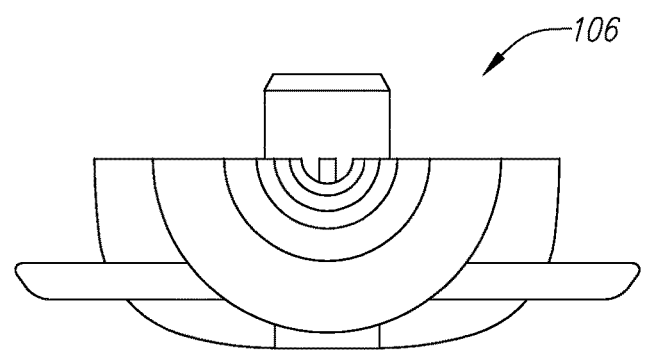
*FIG. 8A*
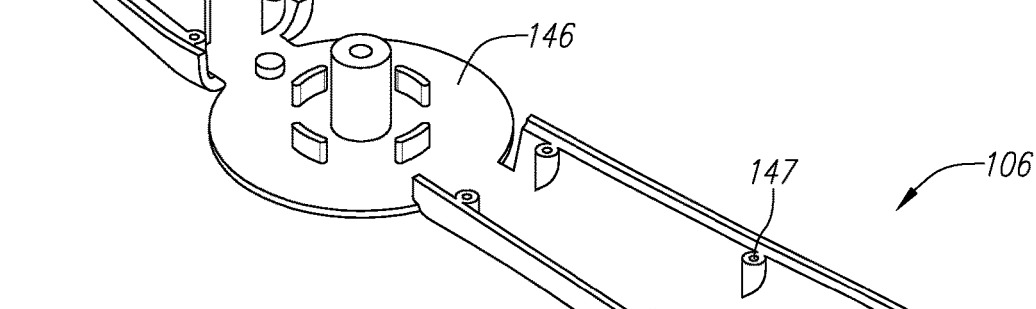
*FIG. 8B*
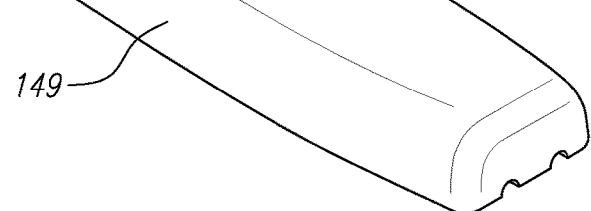
*FIG. 8C*

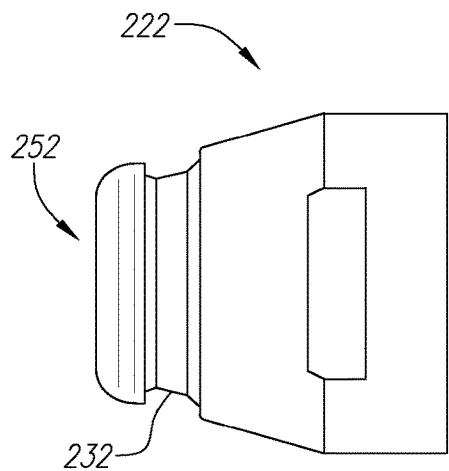 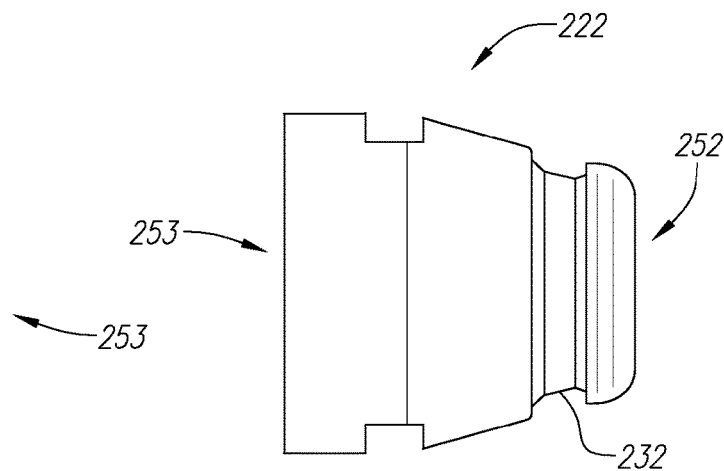
FIG. 9A    FIG. 9B
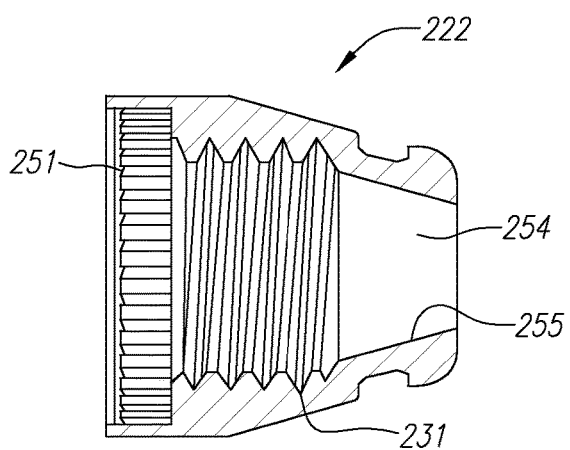 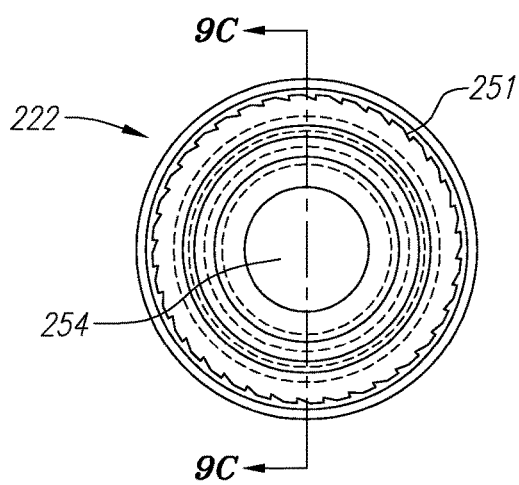
FIG. 9C    FIG. 9D
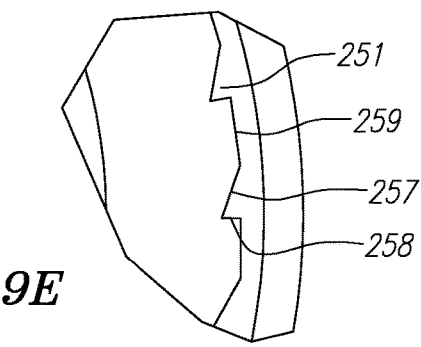
FIG. 9E

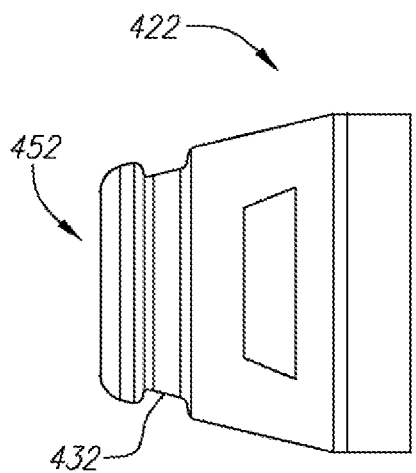
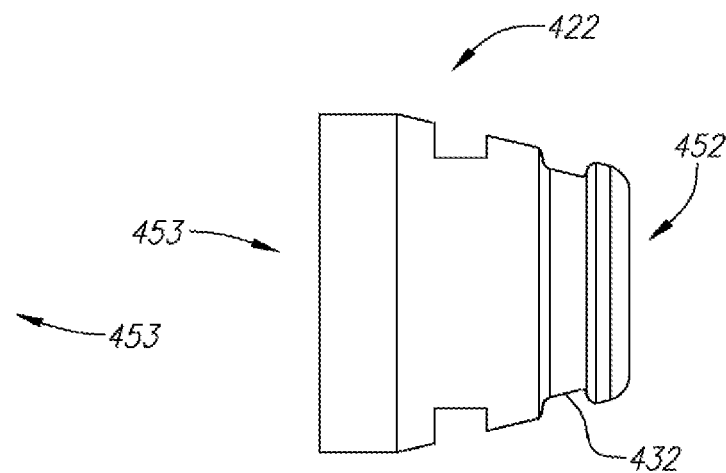
FIG. 11A  FIG. 11B
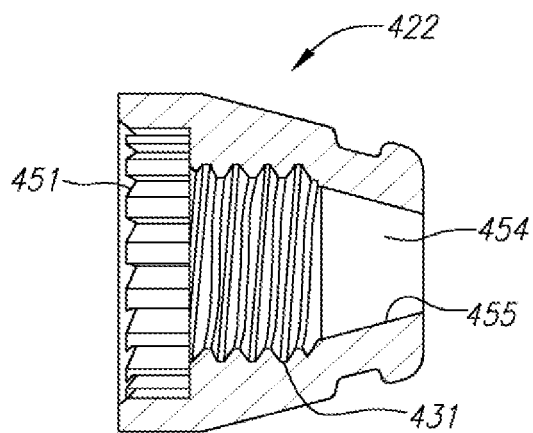
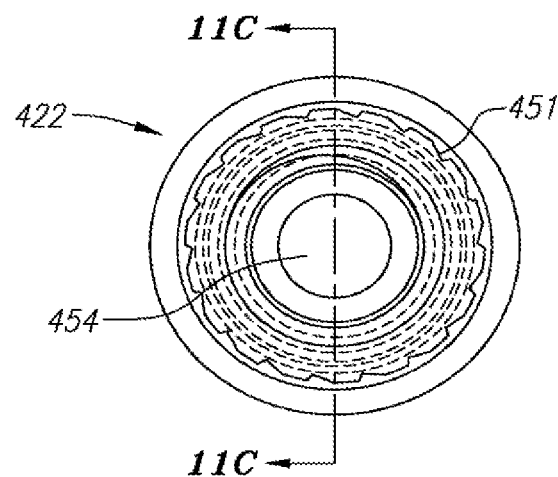
FIG. 11C  FIG. 11D
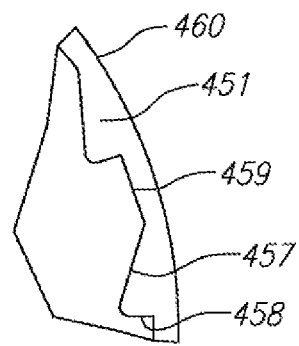
FIG. 11E

THREADED, LOCKING HANDLE MECHANISM FOR ATTACHING TO SHAFT

CROSS-REFERENCE TO RELATED APPLICATIONS

This application claims the benefit of U.S. provisional application No. 61/989,991, filed 7 May 2014, which is hereby incorporated by reference as though fully set forth herein.

BACKGROUND a. Field

This disclosure relates to apparatuses and methods for attaching catheter shafts to handles. In particular, the instant disclosure relates to a mechanism for attaching a catheter shaft to a handle in a way which prevents or at least impedes the handle from being disassembled after being built.

b. Background Art

Electrophysiology catheters are used in a variety of diagnostic and/or therapeutic medical procedures to correct conditions such as atrial arrhythmia, including for example, ectopic atrial tachycardia, atrial fibrillation, and atrial flutter. Arrhythmia can create a variety of dangerous conditions including irregular heart rates, loss of synchronous atrioventricular contractions and stasis of blood flow which can lead to a variety of ailments and even death.

Typically in a procedure, a catheter is manipulated through a patient's vasculature to, for example, a patient's heart, and carries one or more electrodes which may be used for mapping, ablation, diagnosis, or other treatments. Once at the intended site, treatment may include radio frequency (RF) ablation, cryoablation, lasers, chemicals, high-intensity focused ultrasound, etc. An ablation catheter imparts such ablative energy to cardiac tissue to create a lesion in the cardiac tissue. This lesion disrupts undesirable electrical pathways and thereby limits or prevents stray electrical signals that lead to arrhythmias. As readily apparent, such treatment requires precise control of the catheter during manipulation and at the treatment site, which can invariably be a function of a user's skill level.

Prior practice for securing a catheter shaft to a catheter handle comprises using an adhesive with a strain relief or other component to couple the catheter shaft to the handle. The adhesive combined with the strain relief or other component can allow the catheter to be advanced, retracted, and torqued by the catheter handle.

BRIEF SUMMARY

The instant disclosure, in at least one embodiment, relates to a strain relief that can comprise a strain relief projection, and a nut. The nut can comprise a nut thread, a nut recess, a through-hole, and a plurality of ratchets. The strain relief projection can be configured to couple to the nut recess and to secure the nut to the strain relief.

In another embodiment, a catheter assembly can comprise a collet and a strain relief. The collet can comprise a plurality of leaflets, a collet thread, and a plurality of collet spurs. The strain relief can comprise a nut, a nut thread, a through-hole, and a plurality of ratchets. The nut thread and the collet thread can be configured for interaction to screw the strain relief to the collet. The plurality of ratchets can be configured to interact with the plurality of collet spurs to securely fasten the strain relief to the collet. The plurality of leaflets can be configured to securely grip a catheter shaft inserted through the collet and the strain relief In yet another embodiment, a catheter assembly can comprise a catheter handle comprising a collet and a strain relief. The strain relief can comprise a nut and a strain relief projection. The collet can be disposed at a distal end of the catheter handle. The collet can comprise at least one leaflet and at least one collet spur. The nut can comprise at least one ratchet. The collet can be configured to couple to the nut. The at least one ratchet can be configured to interact with the at least one collet spur to securely fasten the strain relief to the catheter handle. The at least one leaflet can also be configured to couple to a catheter shaft.

BRIEF DESCRIPTION OF THE DRAWINGS

FIG. 2 is a top view of a catheter handle including a mechanism for attaching the handle to a catheter shaft FIG. 3 is a longitudinal cross-sectional view taken along line 3-3 of FIG. 2

FIG. 8 is a front view, and two isometric views of a second half of a catheter housing including a mechanism for attaching the handle to a catheter shaft.

FIG. 9 is a side view, another side view rotated 90° and turned 90°, a bottom view, a cross-sectional view taken along line A-A, and a blown up view of the bottom view of a nut in accordance with an embodiment of the disclosure.

FIG. 11 is a side view, another side view rotated 90° and turned 90°, a bottom view, a cross-sectional view taken along line A-A, and a blown up view of the bottom view of a nut in accordance with an embodiment of the disclosure.

DETAILED DESCRIPTION

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Figure 1:
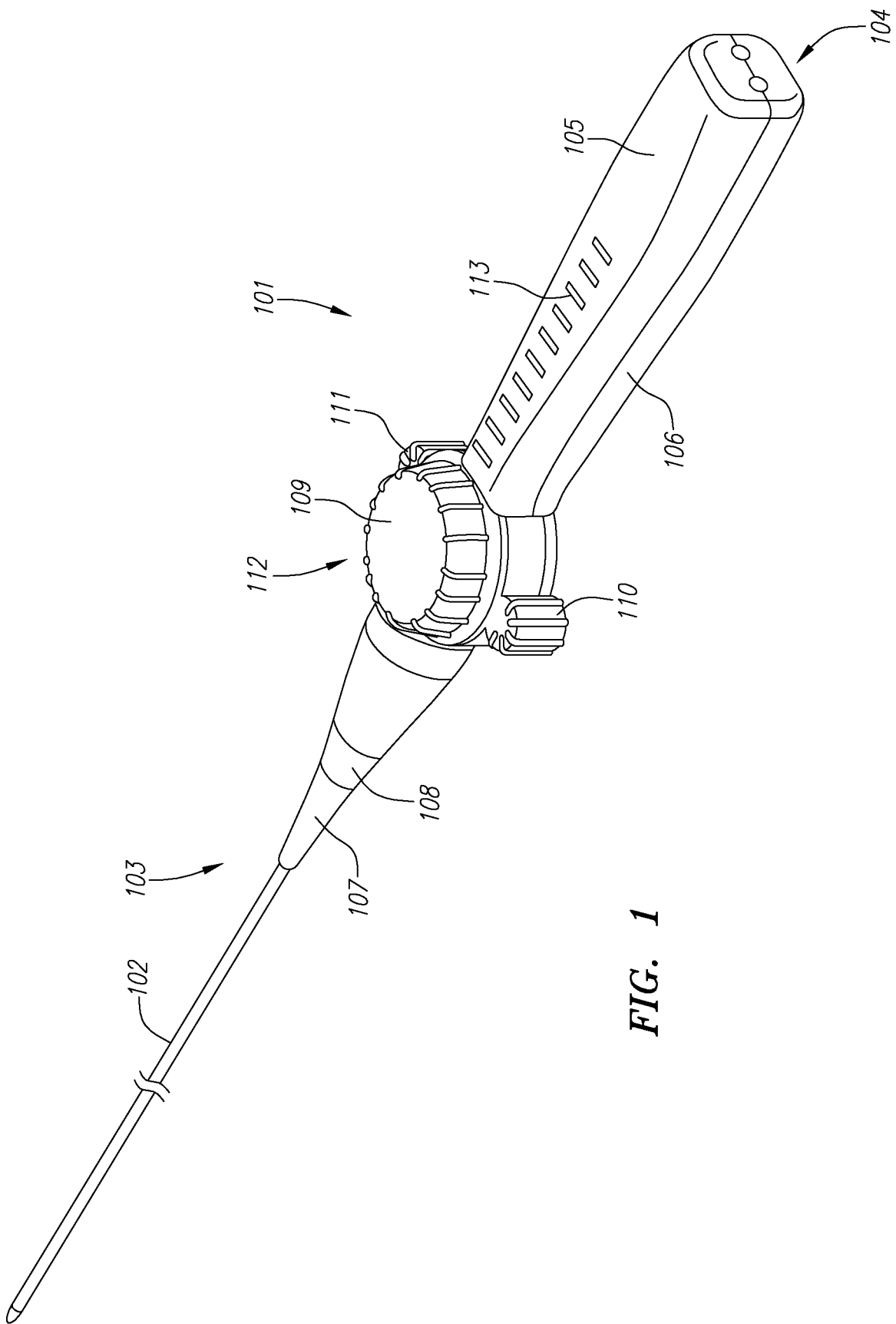
FIG. 1 is an isometric view of a catheter handle having a mechanism for attaching the handle to a catheter shaft

FIG. 1 illustrates one embodiment of a catheter handle configured to manipulate an elongate catheter shaft 102 coupled thereto. The representative catheter handle of FIG. 1 is depicted as a bi-directional catheter, where the catheter shaft can be deflected in two directions, but the principals described herein are equally applicable to uni-directional deflectable catheters, catheters deflectable in more than two directions, fixed catheters that are not steerable, or any catheter where a shaft is attached to a handle. The catheter handle 101 comprises an actuation member 112, a lower handle 106, an upper handle 105, and a strain relief 107. The upper handle 105 and the lower handle 106 can be configured to snap together to form an outer housing for the catheter handle 101. The catheter handle 101 can further comprise a plurality of protrusions 113 that can be made of the same or different materials than the lower handle 106 and the upper handle 105. The plurality of protrusions 113 can be used to improve the tactile feel of the catheter handle 101, to allow a user to more easily determine the angle of the catheter handle 101 without having to look down at their hands, or serve to improve a user's grip on the catheter handle 101. The actuation member 112 can comprise a locking mechanism 109, a first actuation knob 110, and a second actuation knob 111. The locking mechanism 109 can be configured such that when it is turned by a user it causes the actuation member 112 to restrict the movement of the first and second actuation knobs 110, 111. The first actuation knob 110 can be connected to a first pullwire (not shown) that runs through the elongate catheter shaft 102 and is configured to deflect the distal end of the elongate catheter shaft 102. The second actuation knob 111 can be connected to a second pullwire (not shown) that runs through the elongate catheter shaft 102 and is configured to deflect the distal end of the elongate catheter shaft 102 in a second direction. In one embodiment, the first and second pullwires can be configured to deflect the distal end of the elongate catheter shaft 102 in two opposite directions.

A proximal portion 104 of the catheter handle 101 can include connectors for connecting electrical wires to a separate system. The electrical wires can be electrically connected to electrodes or other electro-anatomical sensing and location devices located within the elongate catheter shaft 102. The proximal portion 104 can further comprise connectors for irrigant or other fluid (not shown). The irrigant or other fluid can be fluidly coupled to the elongate catheter shaft 102 and flow therethrough to a distal end of the elongate catheter shaft 102.

The strain relief 107 can be located at a distal portion 103 of the catheter handle 101 and can be configured to securely connect the catheter handle 101 to the elongate catheter shaft 102. The strain relief 107 can be used to securely connect the elongate catheter shaft 102 to the catheter handle 101 as well as reinforcing and providing stability to the proximal portion of the elongate catheter shaft 102. The elongate catheter shaft 102 can be configured to pass through the interior of the strain relief 107. A proximal section 108 of the strain relief 107 can be configured to connect to the upper handle 105 and the lower handle 106 of the catheter handle 101. The strain relief 107 can be made of a stiff but still somewhat flexible material to allow some bending of the elongate catheter shaft in the area it couples to the catheter handle 101.

FIG. 2 illustrates a top down view of the embodiment of the catheter handle 101 in FIG. 1. The upper handle 105 of the catheter handle 101 can be seen in this view. The proximal section 108 of the strain relief 107 can be seen coupled to the upper handle 105. The actuation member 112 comprises the first actuation knob 110 and the second actuation knob 111 offset from each other on opposite sides of the locking mechanism 109. The placement of the plurality of protrusions 113 can also be seen in relation to the upper handle 105.

FIG. 3 shows a cross-section of the catheter handle 101 seen in FIGS. 1 and 2. The cross-section is taken along line 3-3 seen in FIG. 2. The cross-section as seen in FIG. 3 shows the interior of the catheter handle 101 without the elongate catheter shaft, pullwires, and other electrical wires that can be present in a catheter. A more in-depth discussion of the inner workings of the representative actuation member 112 can be found in U.S. Application No. 61/820,613, filed 7 May 2013, (the '613 application) and in U.S. application Ser. No. 14/272,412, filed 7 May 2014, (the '412 application). The '613 application and the '412 application are both hereby incorporated by reference in their entirety as though fully set forth herein. The proximal section 108 of the strain relief 107 comprises a nut 122 that is configured to couple to a collet 118 formed at the distal ends of the upper handle 105 and the lower handle 106. The handle joint 120 forms where the upper handle 105 and the lower handle 106 join.

Figure 4:
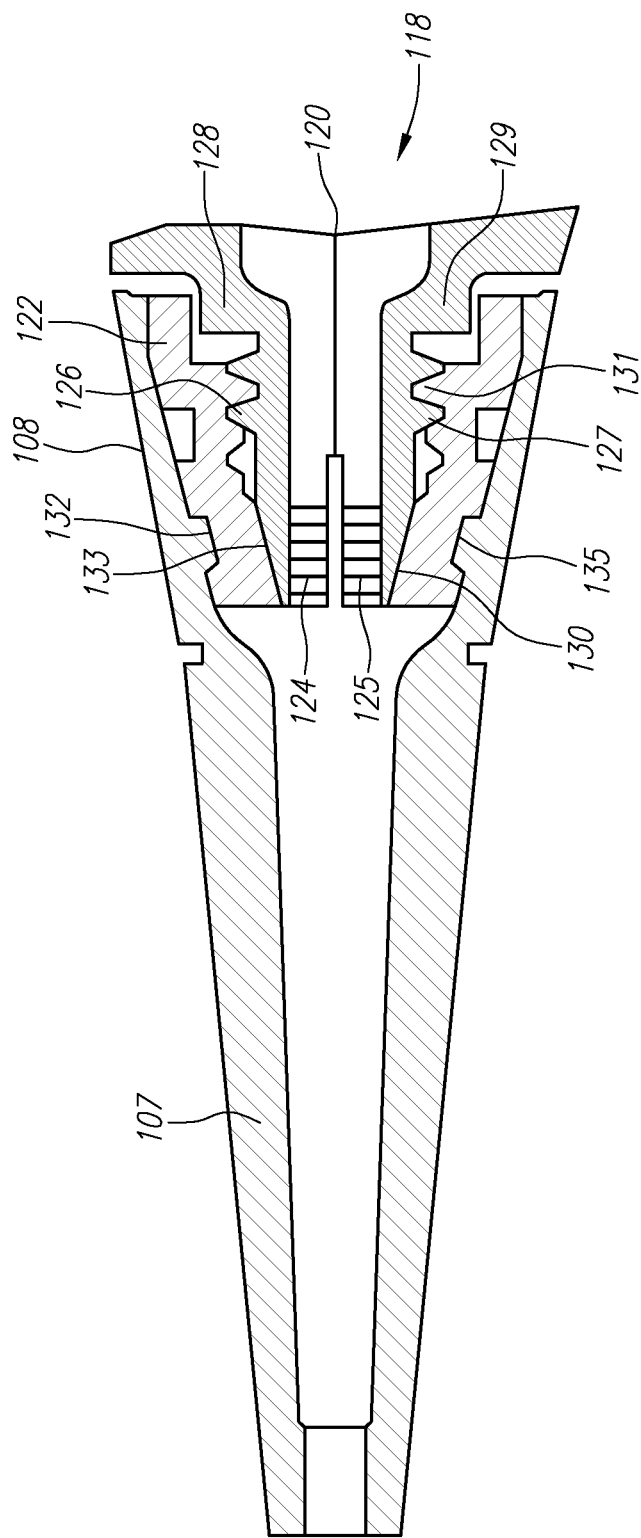
FIG. 4 is an enlarged view of the circled portion labeled FIG. 4 in FIG. 3.

FIG. 4 illustrates a close-up view of the interaction of the strain relief 107 and the collet 118 formed at the distal end of the upper and lower handle 105, 106 as seen in FIG. 3. The interaction of the strain relief 107 and the collet 118 provides a mechanism for attaching a catheter shaft to a catheter handle without adhesive in a way which further impedes or prevents an operator or user from disassembling the catheter handle after it has been built. The collet 118 can comprise two collet halves 128, 129 that can be configured to snap together as described below. In one embodiment each collet half 128, 129 can comprise two leaflets. The collet leaflets can comprise a combination of horizontal and vertical ridges on the inner diameter of the collet 118 to couple the catheter shaft and the collet 118. The horizontal and vertical ridges can grab onto the catheter shaft through friction and compression when the nut 122 is screwed onto the collet 118. The horizontal and vertical ridges can provide a bond to the catheter shaft from the catheter handle and can allow the catheter handle to transmit torque and can also prevent the catheter shaft from sliding relative to the handle. As the nut 122 is threaded onto the collet 118 the leaflets can be cinched down to secure the catheter shaft. The leaflets can be cinched down by the interaction of a tapered edge 133 formed by an interior surface of the nut 122 and a sloped outer surface 130 on the exterior surface of the collet 118. The threads of the nut 122 can align with the threads on the collet 118. The threads of the nut 122 can ensure that the nut 122 is properly aligned with the upper collet half 128 and the lower collet half 129 and ease the attachment of the nut 122 to the collet 118. The lower collet thread 127 and the upper collet thread 126 can be configured to guide the nut 122 for latching onto the ratchets to secure the nut and handle in position on the shaft. As the nut 122 is threaded onto the collet 118, the tapered edge 133 of the nut can close the leaflets of the collet 118 and can trap or secure the catheter shaft within the interior of the collet 118. The nut can be secured to the catheter handle by way of ratchets that are integrally formed on the nut 122. The ratchets can be placed proximally of the threads of the nut 122 and can be configured to interact with the catheter handle proximally of the upper collet thread 126 and the lower collet thread 127. The ratchets can be configured such that the nut can be threaded onto the handle halves in a clockwise direction with a first force, but not be able to be removed from the handle halves with the same first force. When trying to twist the nut 122 in a counter-clockwise direction the ratchets resist movement and a second, greater force would be required to remove the nut 122 from the collet 118. In some embodiments a torque wrench can be used to tighten the nut onto the handle assembly to ensure consistent and complete attachment of the nut 122 to the catheter handle.

The disclosed design of a nut 122 comprising threads and ratchets configured to interact and couple with a collet 118 of a catheter handle can eliminate the need for an adhesive method of attaching the catheter to the handle. It can also allow the torque to be transferred from the handle to the catheter shaft and can also prevent a user or other individual from disassembling the handle after assembly without the use of additional adhesive. Also, by eliminating a need for additional adhesive in the manufacture of the catheter, the process of manufacturing the catheter can be streamlined and the cost reduced. The design disclosed herein can eliminate the need for additional adhesive deployment equipment, curing equipment, and the mess that can be caused by excess adhesive. The design disclosed herein can further reduce the length of time it takes to manufacture a catheter by eliminating the time needed for the adhesive to dry. Another improvement provided by the nut 122 and collet 118 of the disclosure is the ease of verification that the strain relief 107 of the catheter is properly coupled to the catheter handle and that the catheter is properly assembled.

As shown in FIG. 4, the handle joint 120 formed between the upper and lower handles is shown. The handle joint 120 defines the boundary between an upper collet half 128 and a lower collet half 129. The upper collet half 128 can comprise a first upper leaflet 124, a second upper leaflet (not shown), and an upper collet thread 126. The lower collet half 129 can comprise a first lower leaflet 125, a second lower leaflet (not shown), and a lower collet thread 127. The collet 118 is formed by the upper collet half 128 and the lower collet half 129 when the two halves are joined together and the collet 118 is configured such that the upper collet thread 126 and the lower collet thread 127 interact to form a continuous thread that can be configured to interact with a nut 122 coupled to the proximal section 108 of the strain relief 107. The nut comprises a nut thread 131, a nut recess 132, and a plurality of ratchets (See FIGS. 9-12). The nut thread 131 interacts with the upper collet thread 126 and the lower collet thread 127 to couple the nut 122 to the collet 118. The nut 122 is configured to be coupled to the strain relief through interaction between a strain relief projection 135 and the nut recess 132. In some embodiments the nut recess 132 can extend around the circumference of the nut 122. Likewise, in some embodiments the strain relief projection 135 can extend around an inner circumference of the strain relief 107. In other embodiments the nut recess 132 can extend only partially around the nut 122, while the strain relief projection 135 can extend only partially around the inner circumference of the strain relief 107. It is also possible in yet another embodiment that the nut recess 132 can extend around the circumference of the nut 122 while the strain relief projection 135 only extends partially around the inner circumference of the strain relief 107. The strain relief projection 135 can comprise a plurality of separate projections spaced around the inner circumference of the strain relief 107 or be one continuous projection.

Figure 5A:
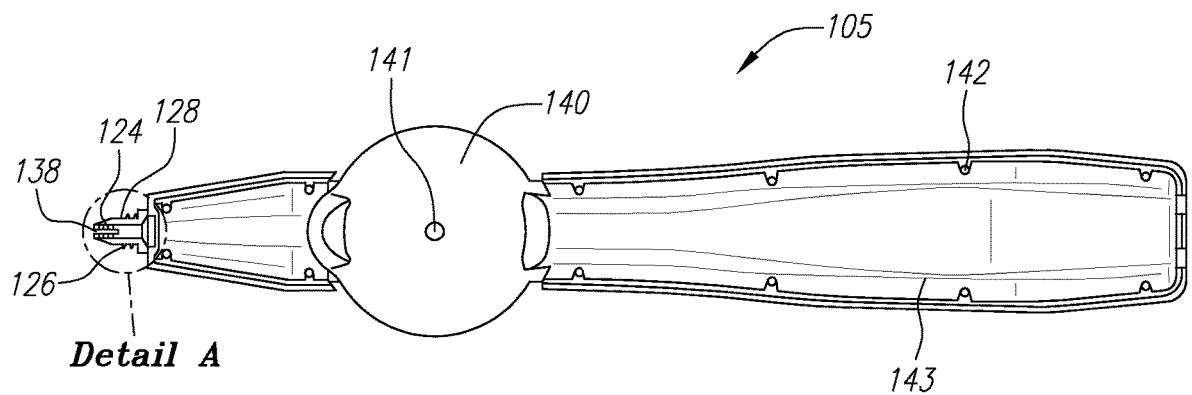
FIG. 5 is a top view, a side view, and a bottom view of a first half of a catheter housing including a mechanism for attaching the handle to a catheter shaft.
Figure 5B:
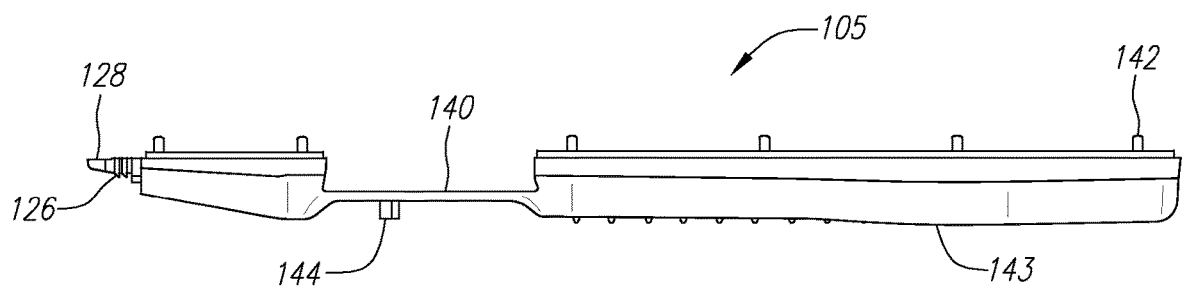
Figure 5C:
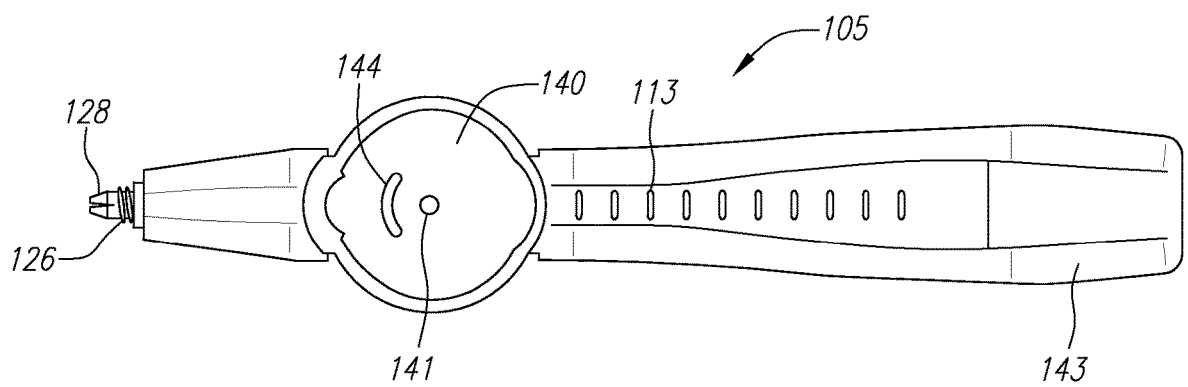
Figure 6A:
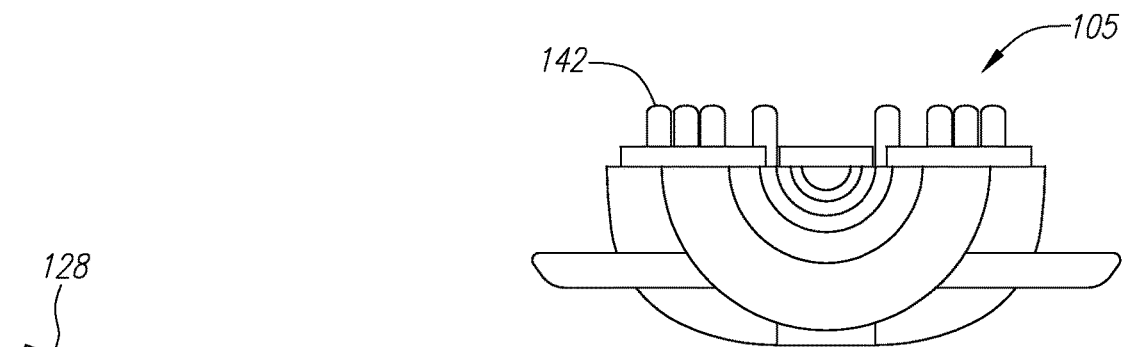
FIG. 6 is a front view, and two isometric views of a first half of a catheter housing including a mechanism for attaching the handle to a catheter shaft.
Figure 6B:
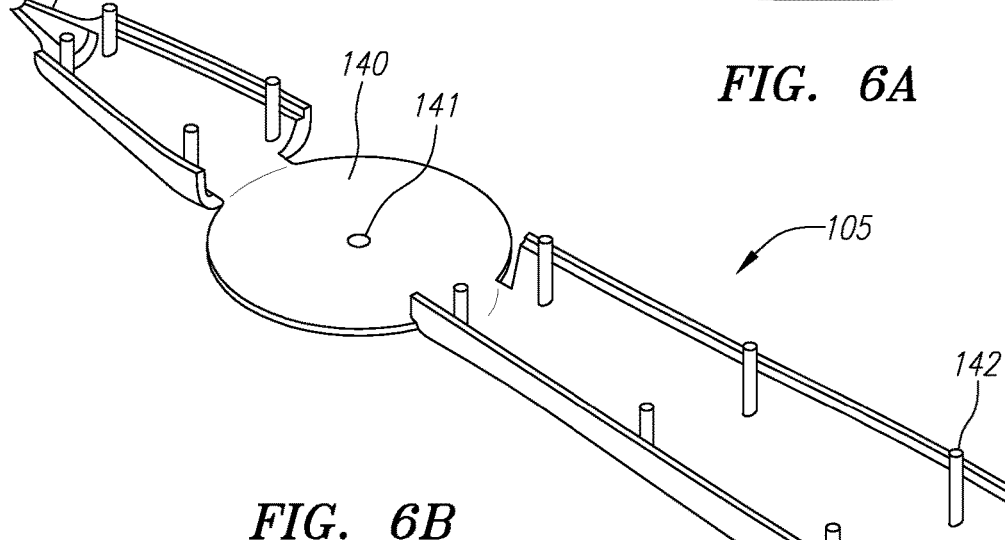
Figure 6C:
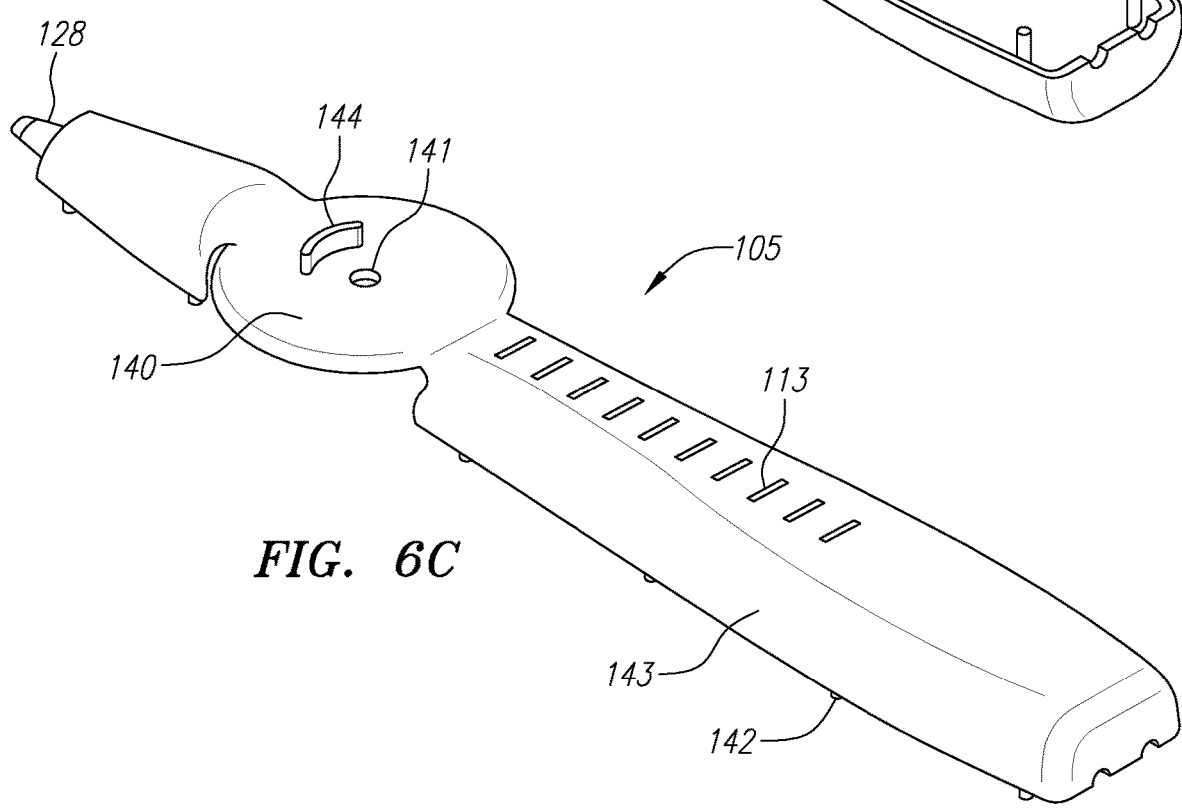

FIGS. 5 and 6 illustrate an embodiment of an upper handle 105. FIG. 5 shows the embodiment of the upper handle 105 from a top view, a side view, and a bottom view. FIG. 6 shows the embodiment of the upper handle 105 from a front view, and isometric side view, and an isometric bottom view. The upper handle 105 comprises an upper collet half 128, an upper handle grip 143, a plurality of protrusions 113, a plurality of joint projections 142, and an upper actuation support 140. The upper handle 105, as illustrated in FIGS. 5 and 6, is configured to be coupled to a lower handle 106, as illustrated in FIGS. 7 and 8.

Figure 7A:
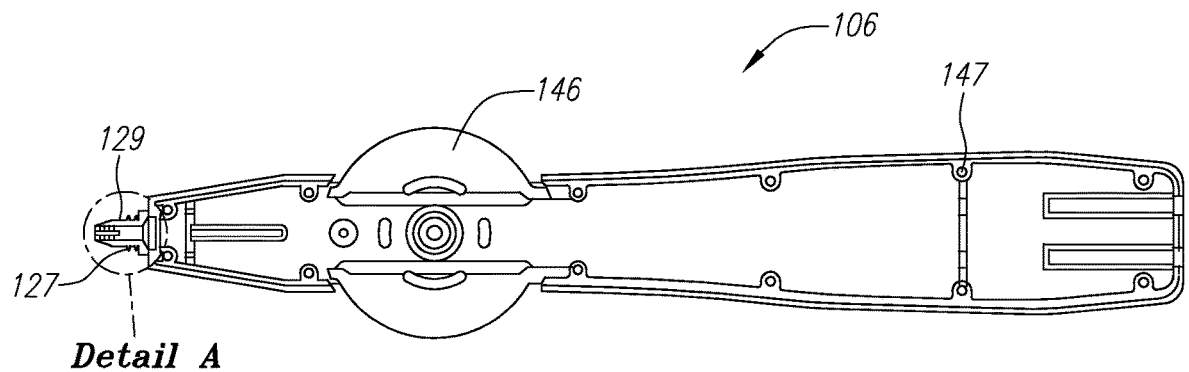
FIG. 7 is a top view, a side view, and a bottom view of a second half of a catheter housing including a mechanism for attaching the handle to a catheter shaft.
Figure 7B:
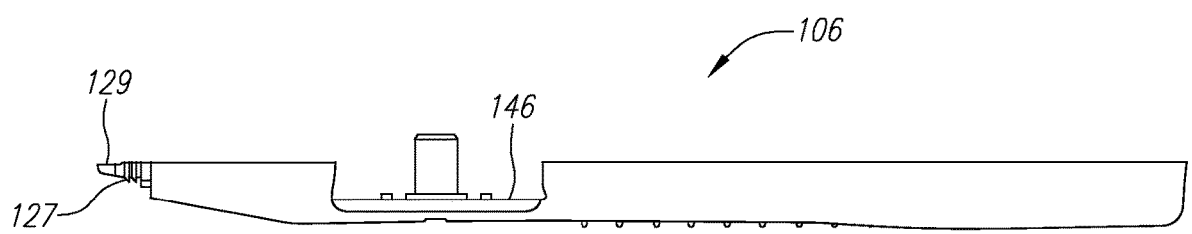
Figure 7C:
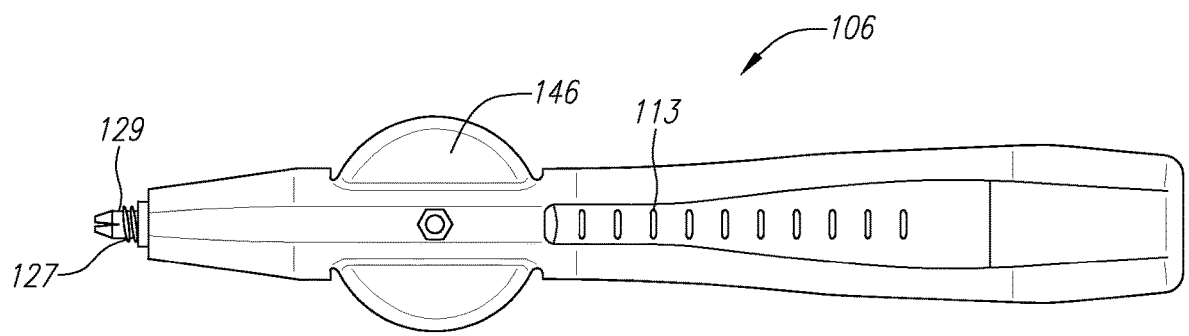

One embodiment of a lower handle can be seen in FIGS. 7 and 8. The upper collet half 128 can further comprise a first upper leaflet 124, a second upper leaflet 138, and an upper collet thread 126. The upper collet half 128 is configured to match up to a lower collet half and form a collet that can be used to securely connect an elongate catheter shaft to a catheter handle formed from the coupled upper handle 105 and lower handle. The upper actuation support 140 comprises a locking pass-through 141 and a locking guide 144. The upper actuation support 140 is configured to support an actuation member coupled thereto. A locking mechanism is configured to engage with the locking guide 144 and mechanically couple to the actuation member through the locking pass-through 141. The plurality of joint projections 142 are configured to couple the upper handle 105 to a lower handle through mechanically coupling with a plurality of docks provided on the lower handle as seen in FIGS. 7 and 8. The number of joint projections 142 provided on the upper handle 105 can vary based on design and manufacturing decisions. In some embodiments the joint projections 142 are configured to connect to the plurality of docks provided on the lower handle in a manner such that the plurality of joint projections 142 cannot be removed from the plurality of docks.

FIG. 9 illustrates a variety of views of an embodiment of a nut 222 according to the disclosure. Starting from the top left of the figure and moving down the page and then to the right the included views of a nut 222 according to the disclosure include a side view, another side view where the nut has been rotated 90° about a longitudinal axis and turned so that a distal end 252 of the nut faces down, a bottom view of the nut 222, a cross-sectional view of the nut 222 taken across line A-A in FIG. 9, and a close up of the outer edge of the nut as illustrated in the bottom view. The exterior of the nut is configured to be fitted within a strain relief as shown in FIG. 4. A nut recess 232 can be configured to interact or couple with a strain relief to secure the nut 222 to the strain relief. The nut recess 232 can be a depression that runs around an outer circumference of the nut 222. In other embodiments the nut recess 232 can comprise spaced holes that can be configured to interact with corresponding protrusions, other extensions, or designs present on the strain relief to couple the nut 222 to the strain relief In yet other embodiments the nut can comprise a bulging or protruding portion either in replacement to or in addition of the nut recess 232 to allow interaction or coupling between the nut 222 and the strain relief.

The bottom view of the nut 222 illustrates the through-hole 254 that passes from a proximal end 253 to the distal end 252 of the nut 222. The through-hole 254 is configured to receive the collet and leaflets of the catheter handle (shown in FIGS. 4 and 13A-15B). The distal end 252 of the through-hole 254 is sized and configured to allow the passage of a catheter shaft therethrough. As seen in the bottom view and cross-sectional view of the nut 222 the ratchets 251 can be placed in a continuous ring on the interior of the nut 222 and can be adjacent to a proximal end 253 of the nut 222. The ratchets 251 can be configured to interact with corresponding collet spurs (shown in FIGS. 13A-15B). The far right illustration in FIG. 9 shows a blow up view of several of the ratchets 251 present along the ring adjacent the proximal end of the nut 222 in the embodiment. The ratchets 251 can be designed to interact with a plurality of collet spurs on the collet. The ratchets 251 can be configured to twist on to the collet with a first force, and only be removable with a second larger force. In the current embodiment the ratchets 251 can comprise a sloping portion 257 that can interact with the collet spurs as the nut 222 is coupled to the collet, and a resisting portion 258 that can interact with the collet spurs if an attempt is made to remove the nut 222 from the collet. In the current embodiment the resisting portion forms around a 90° angle with an inner surface 259 of the nut 222. The sloping portion 257 of the ratchets 251 can comprise various angles that can allow for the nut 222 to be coupled to a collet or a catheter handle. The space between the ratchets 251 can be of various distances along the inner surface of the nut 222. The number of ratchets 251 and spacing between ratchets 251 can vary based on desired design and the amount of force desired to remove the nut 222 from the collet or catheter handle it is designed to be coupled to. In other embodiments, the ratchets 251 can be intermittently spaced along the interior of the nut 222. It is also disclosed that the ratchets can be present in a continuous ring or intermittently spaced in other areas of the nut 222. It is also disclosed that the collet can comprise the ratchets currently illustrated on an interior surface of the nut 222 and the collet spurs that are configured to interact and lock with the ratchets 251 can be present on the nut 222. As illustrated in the cross-sectional view taken along line A-A, the nut 222 further comprises a nut thread 231 and a tapered edge 255.

Figures 10A, 10B:
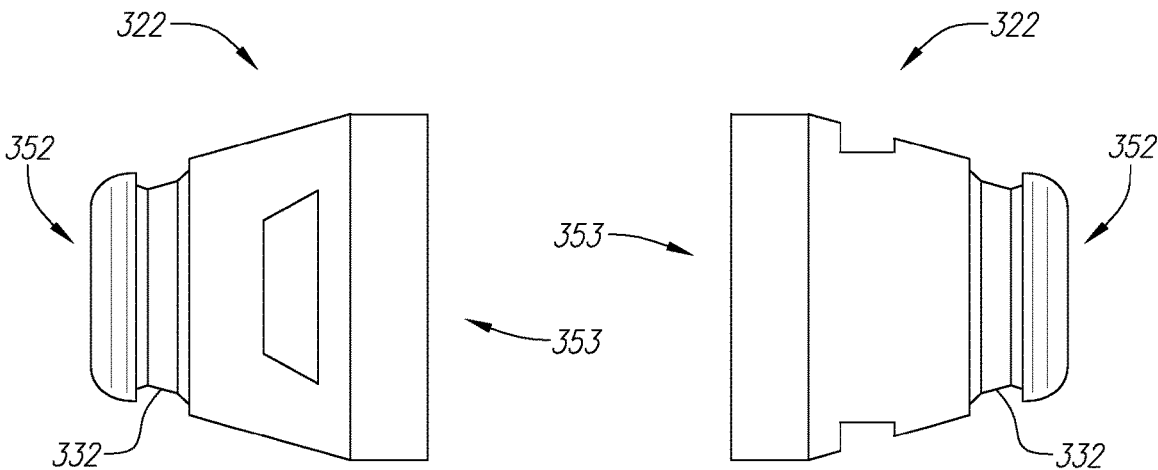
FIG. 10 is a side view, another side view rotated 90° and turned 90°, a bottom view, a cross-sectional view taken along line A-A, and a blown up view of the bottom view of a nut in accordance with an embodiment of the disclosure.
Figures 10C, 10D:
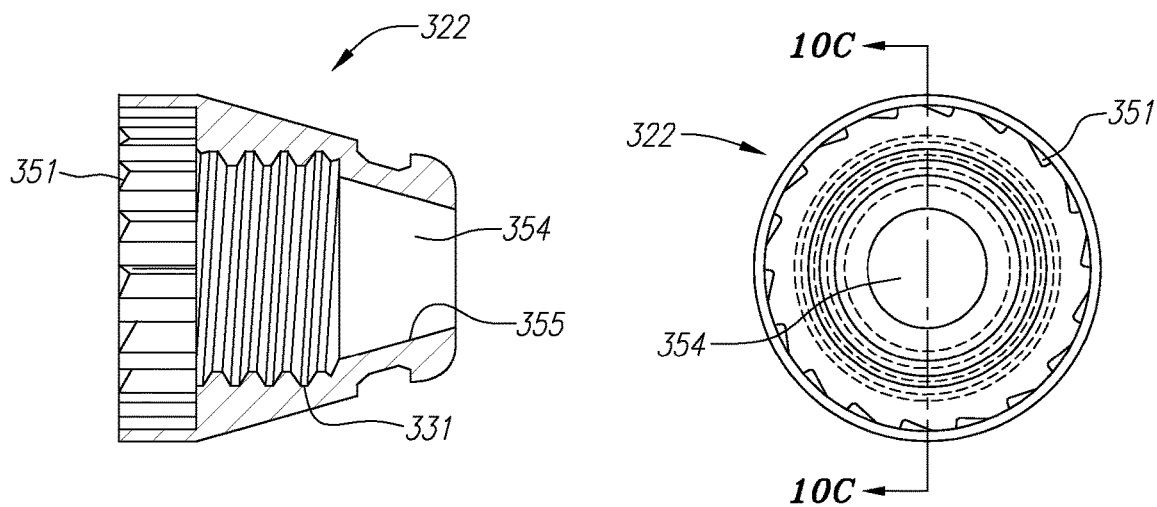
Figure 10E:
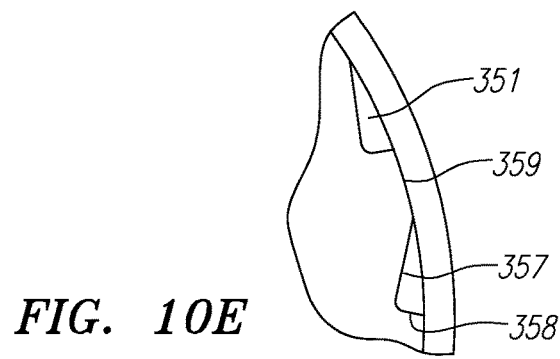
Figure 12A:
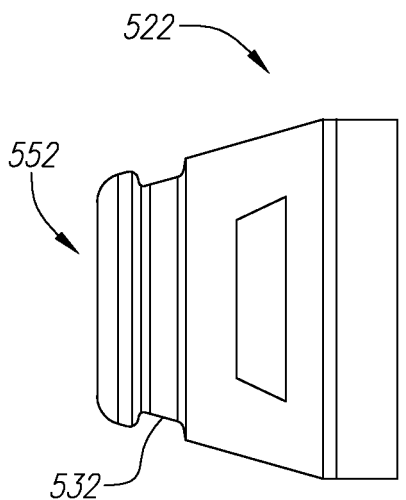
FIG. 12 is a side view, another side view rotated 90° and turned 90°, a bottom view, a cross-sectional view taken along line A-A, and a blown up view of the bottom view of a nut in accordance with an embodiment of the disclosure.
Figure 12B:
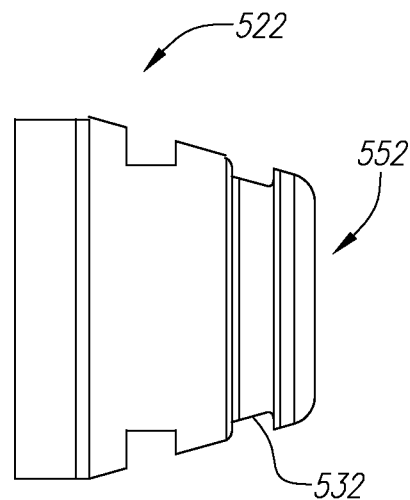
Figure 12C:
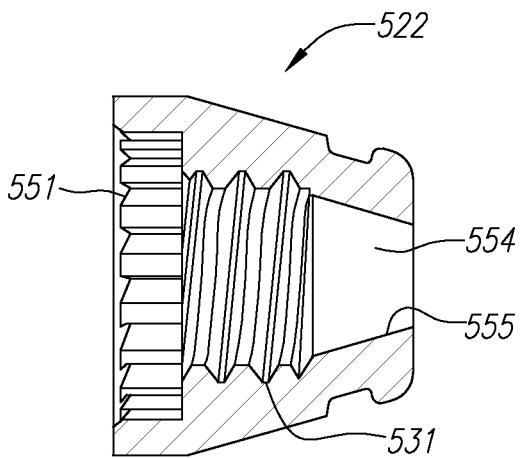
Figure 12D:
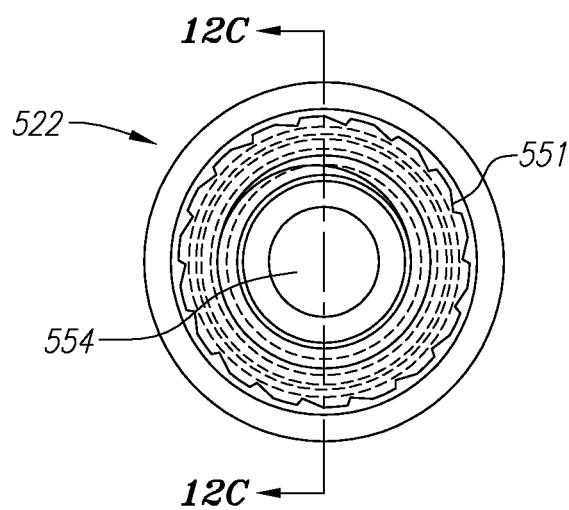
Figure 12E:
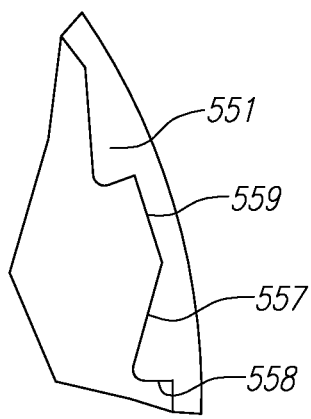

FIG. 10 illustrates a variety of views of another embodiment of a nut 322 according to the disclosure. Starting from the top left of the figure and moving down the page and then to the right the included views of a nut 322 according to the disclosure include a side view, another side view where the nut has been rotated 90° about a longitudinal axis and turned so that a distal end 352 of the nut faces down, a bottom view of the nut 322, a cross-sectional view of the nut 322 taken across line A-A in FIG. 10, and a close up of the outer edge of the nut as illustrated in the bottom view. FIG. 10 discloses another design of the ratchets 351 disclosed herein. In the illustrated embodiment the nut 322 is thinner where the ratchets are present and the ratchets show another design that can be used in the disclosure. Stated another way, an inner surface 359 of the nut 322 is closer to an outer surface of the nut 322 in the current embodiment. In the illustrated design, where the resisting portion 358 and the sloping portion 357 meet the corner is more sloped and not as abrupt as that seen in FIG. 9. In some embodiments this design can ease construction or performance of the nut 322. The nut 322 can comprise a distal end 352, a proximal end 353, and a nut recess 332 as discussed in relation to FIG. 9. The nut can further comprise a through-hole 354, a tapered edge 355, and a nut thread 331 as discussed in relation to FIG. 9.

FIG. 11 illustrates a variety of views of yet another embodiment of a nut 422 according to the disclosure. Starting from the top left of the figure and moving down the page and then to the right the included views of a nut 422 according to the disclosure include a side view, another side view where the nut has been rotated 90° about a longitudinal axis and turned so that a distal end 452 of the nut faces down, a bottom view of the nut 422, a cross-sectional view of the nut 422 taken across line A-A in FIG. 11, and a close up of the outer edge of the nut as illustrated in the bottom view. FIG. 11 discloses another design of the ratchets 451 disclosed herein. In the illustrated example the nut is around the same thickness as that seen in FIG. 9, however, the shape of the ratchets 451 is similar to that shown in FIG. 10. As shown in FIG. 11, the resisting portion 458 and the sloping portion 457 of each of the ratchets 451 meets in a corner that is more sloped or rounded. In the illustrated embodiment the resisting portion 458 of the ratchets 451 forms about a 90° angle with an inner surface 459. In another embodiment of the disclosure the ratchets 451 can comprise a varying configuration around the inner surface 459 of the nut 422. The ratchets 451 can be designed to be different every other, in sections, or in other ways as would be apparent to one of ordinary skill in the art. The nut 422 can comprise a distal end 452, a proximal end 453, and a nut recess 432 as discussed in relation to FIG. 9. The nut can further comprise a through-hole 454, a tapered edge 455, and a nut thread 431 as discussed in relation to FIG. 9.

FIG. 12 illustrates a variety of views of another embodiment of a nut 522 according to the disclosure. Starting from the top left of the figure and moving down the page and then to the right the included views of a nut 522 according to the disclosure include a side view, another side view where the nut has been rotated 90° about a longitudinal axis and turned so that a distal end 552 of the nut faces down, a bottom view of the nut 522, a cross-sectional view of the nut 522 taken across line A-A in FIG. 10, and a close up of the outer edge of the nut as illustrated in the bottom view. FIG. 12 discloses a nut that has been optimized for injection molding. In the illustrated embodiment the nut threads 531 can be seen to be fewer and more robust than those shown in FIGS. 9-11. The thickness of the nut can also be increased to ease manufacture using injection molding. The ratchets 551 illustrated in FIG. 12 are similar to those shown in FIG. 11 with similar sloping portion 557, resisting portion 558, and inner surface 559, but any ratchet design disclosed herein can be used in a nut 522 created through injection molding. The use of injection molding can reduce costs of the components of the catheter and ease manufacture. The nut 522 can comprise a distal end 552, a proximal end 553, and a nut recess 532 as discussed in relation to FIG. 9. The nut can further comprise a through-hole 554 and a tapered edge 555, as discussed in relation to FIG. 9

Figure 13A:
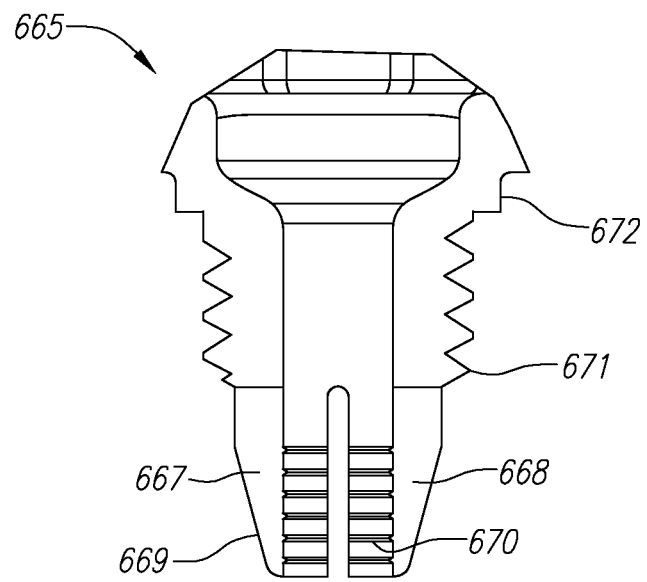
FIG. 13A is a top view of a first collet half in accordance with an embodiment of the disclosure.
Figure 13B:
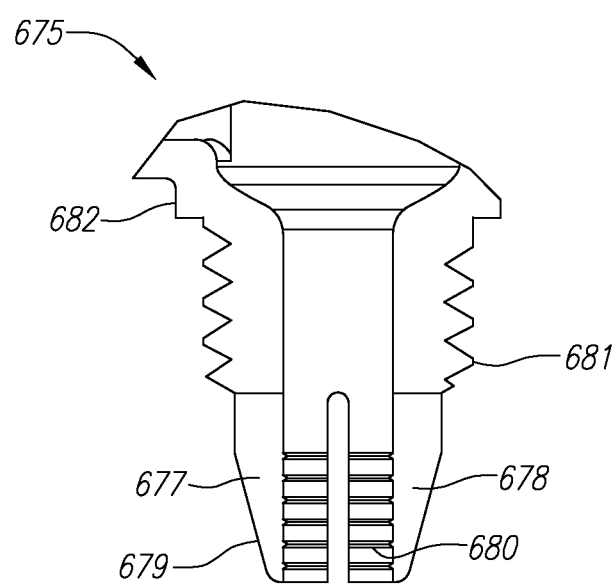
FIG. 13B is a top view of a second collet half in accordance with an embodiment of the disclosure.

FIGS. 13A and 13B illustrates an embodiment of a first collet half 665 and a second collet half 675 that are configured to be coupled together as shown in FIGS. 1-8 to form a combined collet. The first collet half 665 comprises a first leaflet 667, a second leaflet 668, a first collet thread 671, a plurality of first horizontal ridges 670, a sloped outer surface 669, and a plurality of first collet spurs 672. The second collet half 675 comprises a third leaflet 677, a fourth leaflet 678, a second collet thread 681, a plurality of second horizontal ridges 680, a sloped outer surface, and a plurality of second collet spurs 682. When the first collet half 665 and the second collet half 675 are coupled together as discussed previously in the disclosure the various like pieces match to form a contiguous whole that can be used to secure a catheter shaft to a catheter handle or to couple the integrated catheter handle or collet to a nut and accompanying strain relief as shown in FIGS. 1-8. The first collet thread 671 and the second collet thread 681 meet to form a contiguous thread that a nut, such as those illustrated in FIGS. 9-12, can be can be threaded onto. In the embodiment illustrated in FIGS. 13A and 13B the first, second, third, and fourth leaflets 667, 668, 677, 678 are configured to securely grip or fasten the combined collet to a catheter shaft. The leaflets are pressed into the catheter shaft when a nut is fastened and secured to the combined collet and in the process interacts with the sloped outer surface 679 of the combined collet. When the leaflets are pressed into the catheter shaft a plurality of first horizontal ridges 670 and second horizontal ridges 680 are pressed into the catheter shaft and assist in securing the catheter shaft to the combined collet so that a catheter handle can advance, retract, or impart torque to the catheter shaft. The first collet half 665 and the second collet half 675 can further comprise first collet spurs 672 and second collet spurs 682. The collet spurs are configured to interact and secure a plurality of ratchets that can be present on a nut as discussed in the disclosure. The design of the collet spurs can vary. In some cases the design of the collet spurs is the same as the ratchets, but going in the opposite direction such that when the nut is secured to the combined collet the resisting portion of the nut is matched with a resisting portion of the collet and removal of the nut is impeded.

Figure 14A:
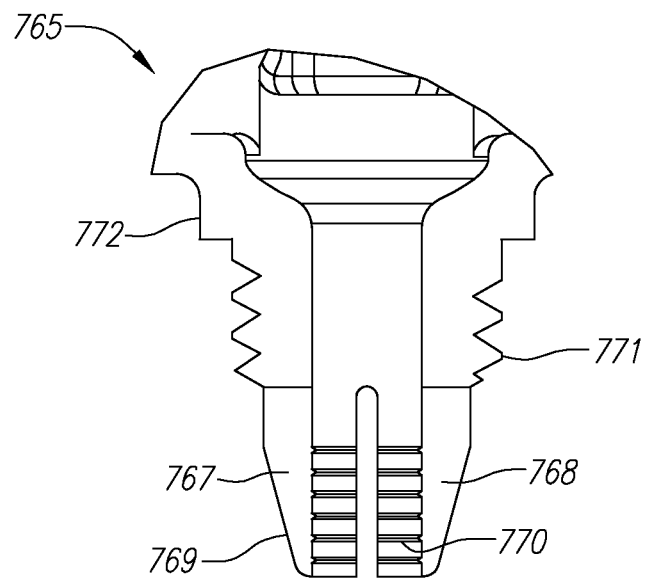
FIG. 14A is a top view of a first collet half in accordance with an embodiment of the disclosure.
Figure 14B:
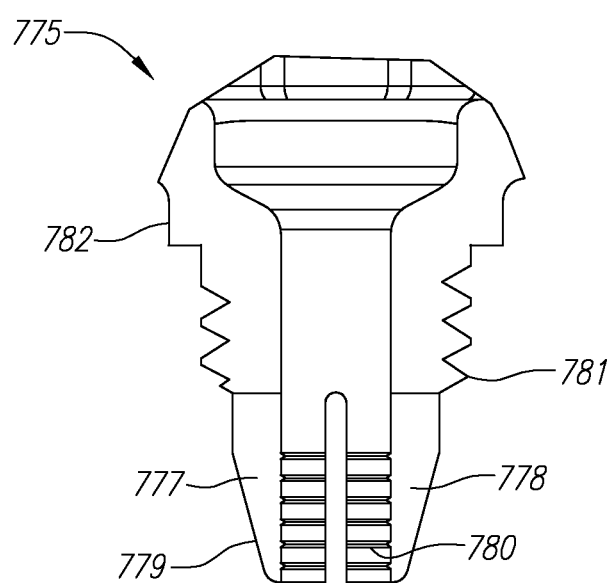
FIG. 14B is a top view of a second collet half in accordance with an embodiment of the disclosure.

FIGS. 14A and 14B illustrates another embodiment of a first collet half 765 and a second collet half 775 that are configured to be coupled together as shown in FIGS. 1-8 to form a combined collet. The first collet half 765 comprises a first leaflet 767, a second leaflet, a first collet thread 771, a plurality of first horizontal ridges, a sloped outer surface 769, and a plurality of first collet spurs 772. The second collet half 775 comprises a third leaflet 777, a fourth leaflet 778, a second collet thread 781, a plurality of second horizontal ridges 780, a sloped outer surface, and a plurality of second collet spurs 782. When the first collet half 765 and the second collet half 775 are coupled together as discussed previously in the disclosure the various like pieces match to form a contiguous whole that can be used to secure a catheter shaft to a catheter handle or to couple the integrated catheter handle or collet to a nut and accompanying strain relief as shown in FIGS. 1-8. The embodiment disclosed in FIGS. 14A and 14B is similar to that illustrated in FIGS. 13A and 13B, however, in the illustrated embodiment the first collet thread 771 and the second collet thread 781 and the resulting combined collet thread have a different configuration than that shown in FIGS. 13A and 1313. The combined first collet thread 771, the second collet thread 781, and the combined collet thread in the current embodiment comprises more turns around the collet.

Figure 15A:
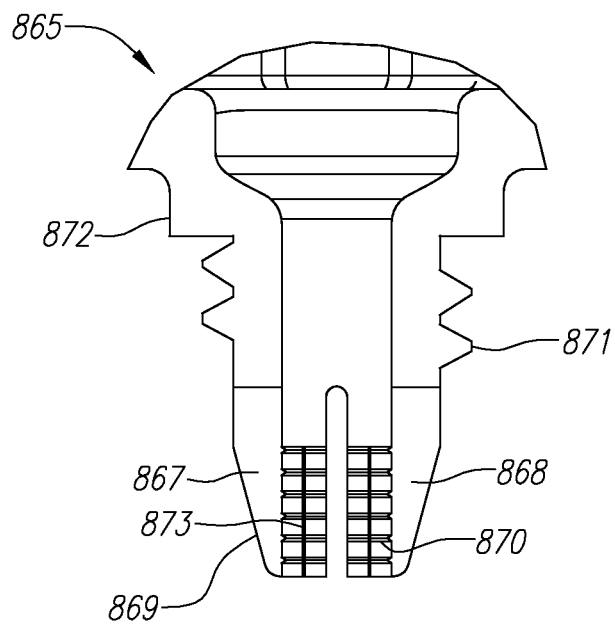
FIG. 15A is a top view of a first collet half in accordance with an embodiment of the disclosure.
Figure 15B:
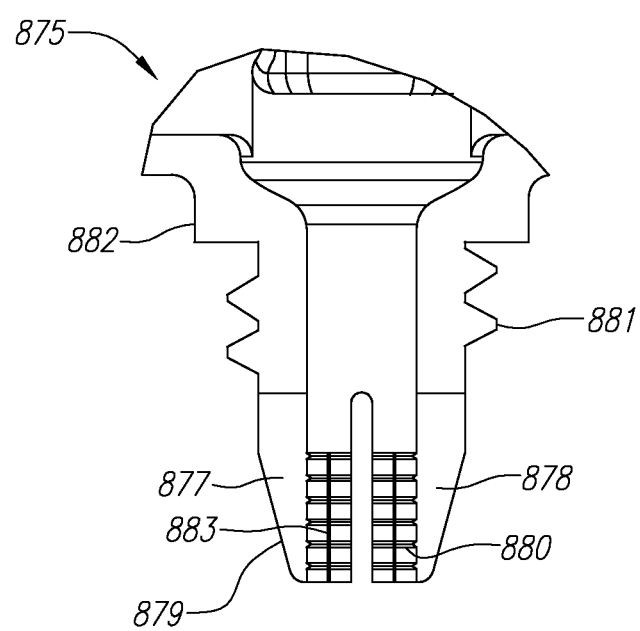
FIG. 15B is a top view of a second collet half in accordance with an embodiment of the disclosure.

FIGS. 15A and 15B illustrates yet an embodiment of a first collet half 865 and a second collet half 875 that are configured to be coupled together as shown in FIGS. 1-8 to form a combined collet. The first collet half 865 comprises a first leaflet 867, a second leaflet 868, a first collet thread 871, a plurality of first horizontal ridges 870, a sloped outer surface 869, and a plurality of first collet spurs 872. The second collet half 875 comprises a third leaflet 877, a fourth leaflet 878, a second collet thread 881, a plurality of second horizontal ridges 880, a sloped outer surface 879, and a plurality of second collet spurs 882. When the first collet half 865 and the second collet half 875 are coupled together as discussed previously in the disclosure the various like pieces match to form a contiguous whole that can be used to secure a catheter shaft to a catheter handle or to couple the integrated catheter handle or collet to a nut and accompanying strain relief as shown in FIGS. 1-8. The embodiment disclosed in FIGS. 15A and 1513 is similar to those illustrated in FIGS. 13A through 1413, however, in the illustrated embodiment the first collet thread 871 and the second collet thread 881 and the resulting combined collet thread have a different configuration than those shown in FIGS. 13A through 4B. In the illustrated embodiment the first collet thread 871 and the second collet thread 881 are formed robustly enough such that the first collet half 865 and the second collet half 875 can be injection molded as discussed above in relation to FIG. 12. The embodiment illustrated in FIGS. 15A and 15B further comprises at least one vertical ridge 883. The at least one vertical ridge 883 can assist in securing the catheter shaft to the collet and by extension the catheter handle. The number of vertical ridges 883 can vary in different embodiments and can vary from a single vertical ridge 883 present on one of the plurality of leaflets to one or more vertical ridges 883 present on each of the plurality of leaflets. While the vertical ridges 883 are only illustrated in relation to FIGS. 15A and 15B, they can be included in any of the designs disclosed herein.

The design of the various embodiments of nuts, upper handles, and lower handles, can be optimized for injection molding. Configuring the various components to be injection molded can reduce costs. The various components can be optimized for injection molding by increasing the wall thickness and optimizing the threads. The designs as disclosed herein can also be designed to be machined to achieve the desired dimensions and forms. In one embodiment, the designs disclosed herein comprise a material with a sufficient hardness such that the threads, the collet threads, the collet ridges, and the ratchets can maintain their form and not wear. One example of a material that could be used for these components is ABS. Other appropriate materials would be known to one of ordinary skill in the art.

Although at least one embodiment of a locking handle mechanism for attaching a shaft has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and can include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure can be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A strain relief, comprising:
   a strain relief projection extending around a complete inner circumference of the strain relief; and
   a nut comprising:
   a nut thread;
   a nut recess extending around a complete outer circumference of the nut;
   a through-hole; and
   a plurality of ratchets,
   wherein the strain relief projection is configured to couple to the nut recess and to secure the nut to the strain relief.

2. The strain relief according to claim 1, wherein the nut further comprises a tapered edge that is configured for interaction with a catheter handle.

3. The strain relief according to claim 1, wherein at least one of the plurality of ratchets comprises a resisting portion and a sloping portion.

4. The strain relief according to claim 1, wherein the plurality of ratchets comprises a plurality of differently shaped ratchets.

5. The strain relief according to claim 1, wherein the strain relief is further configured to interact with the distal end of a catheter handle to secure a catheter shaft to the catheter handle.

6. The strain relief according to claim 1, wherein the strain relief projection is one of a plurality of strain relief projections.

7. A catheter assembly, comprising;
   a collet comprising:
   a plurality of leaflets comprising ridges on the internal surface of the collet;
   a collet thread; and
   a plurality of collet spurs;
   a strain relief comprising:
   a nut;
   a nut thread;
   a through-hole; and
   a plurality of ratchets
   wherein the nut thread and the collet thread are configured for interaction to screw the strain relief to the collet, wherein the plurality of ratchets are configured to interact with the plurality of collet spurs to securely fasten the strain relief to the collet, and wherein the plurality of leaflets are configured to securely grip a catheter shaft inserted through the collet and the strain relief.

8. The catheter assembly according to claim 7, wherein the strain relief further comprises a tapered edge and the collet further comprises a sloped outer surface and wherein the tapered edge is configured to interact with the sloped outer edge to press the plurality of leaflets into the catheter shaft.

9. The catheter assembly according to claim 7, further comprising a catheter handle coupled to a proximal end of the collet.

10. The catheter assembly according to claim 9, wherein the collet is further configured to transmit a torque imparted to the catheter handle to the catheter shaft.

11. The catheter assembly according to claim 7, wherein the nut further comprises a tapered edge that is configured fur interaction with a catheter handle.

12. A catheter assembly, comprising:
    a catheter handle comprising a collet; and
    a strain relief comprising a nut and a strain relief projection,
    wherein the collet is disposed at a distal end of the catheter handle, wherein the collet comprises at least one leaflet comprising internal ridges and at least one collet spur, wherein the nut comprises at least one ratchet, wherein the collet is configured to couple to the nut, wherein the at least one ratchet is configured to interact with the at least one collet spur to securely fasten the strain relief to the catheter handle, and wherein the at least one leaflet is configured to couple to a catheter shaft.

13. The catheter assembly according to claim 12, wherein the collet further comprises a collet thread, wherein the strain relief further comprises a nut thread, and wherein the nut thread and the collet thread are configured to couple the collet and the strain relief.

14. The catheter assembly according to claim 12, wherein the at least one leaflet is configured to transmit a torque imparted to the catheter handle to the catheter shaft.

15. The catheter assembly according to claim 12, wherein the nut further comprises a tapered edge that is configured for interaction with the catheter handle.

* * * * *